(12) United States Patent
Gabriel

(10) Patent No.: US 10,987,098 B2
(45) Date of Patent: Apr. 27, 2021

(54) Z-SHAPED MENISCUS REPAIR DEVICE AND METHOD

(71) Applicant: Rodney Albert Gabriel, Los Angeles, CA (US)

(72) Inventor: Rodney Albert Gabriel, Los Angeles, CA (US)

(*) Notice: Subject to any disclaimer, the term of this patent is extended or adjusted under 35 U.S.C. 154(b) by 0 days.

(21) Appl. No.: 16/911,351

(22) Filed: Jun. 24, 2020

(65) Prior Publication Data

US 2020/0405287 A1 Dec. 31, 2020

Related U.S. Application Data

(60) Provisional application No. 62/867,170, filed on Jun. 26, 2019.

(51) Int. Cl.
| | |
|---|---|
| *A61B 17/04* | (2006.01) |
| *A61B 17/06* | (2006.01) |
| *A61F 2/30* | (2006.01) |

(52) U.S. Cl.
CPC .... *A61B 17/0469* (2013.01); *A61B 17/06066* (2013.01); *A61B 17/06166* (2013.01); *A61B 17/0467* (2013.01); *A61F 2/30756* (2013.01)

(58) Field of Classification Search
CPC . A61B 17/0469; A61B 17/0485; A61B 1/317; A61B 17/16; A61B 17/1675; A61B 17/1764
See application file for complete search history.

(56) References Cited

U.S. PATENT DOCUMENTS

| | | | |
|---|---|---|---|
| 6,893,448 B2* | 5/2005 | O'Quinn | A61B 17/0469 606/139 |
| 8,460,318 B2 | 6/2013 | Murray et al. | |
| 9,486,208 B2* | 11/2016 | Baird | A61B 17/0491 |

(Continued)

OTHER PUBLICATIONS

Catherine Laible, MD, et al., entitled "Meniscal Repair" published in the Journal of the American Academy of Orthopaedic Surgeons, Apr. 2013, vol. 21, No. 4, pp. 204-213.

(Continued)

*Primary Examiner* — Sarah W Aleman
(74) *Attorney, Agent, or Firm* — William J. Benman; Benman, Brown & Williams

(57) ABSTRACT

A z-shaped surgical device including a handle and a rod secured to the handle having: a first elongate segment at a proximal end thereof; a second elongate segment angled with respect to the first segment; and a third elongate segment angled with respect to the second segment. In the illustrative application, the invention provides an arthroscopic meniscus tissue repair suture passer device that penetrates tissue with its distal tip in one direction and utilizes a needle or similar part to penetrate tissue in the opposite direction placing a suture around the torn tissue. The device has an extended z-shaped shape distally that facilitates placement of a suture around torn meniscus tissue with a novel single stroke relative to the prior art. The z-shaped angles are extended for improved access, maneuverability and passage of the device to and through tissue including but not limited to meniscus and other tissue, around meniscus and other tissue, into open and tight spaces between joints and other bodily spaces, and in difficult to access spaces in joints and other compartments.

19 Claims, 7 Drawing Sheets

(56) References Cited

U.S. PATENT DOCUMENTS

2011/0295279 A1* 12/2011 Stone ................. A61B 17/0469
  606/145
2018/0256160 A1* 9/2018 Kurd ................ A61B 17/06133

OTHER PUBLICATIONS https://www.arthrex.com/knee/knee-scorpion.
https://www.youtube.com/watch?v=Dh6JDZ8kYOk&feature=youtu.be.

* cited by examiner

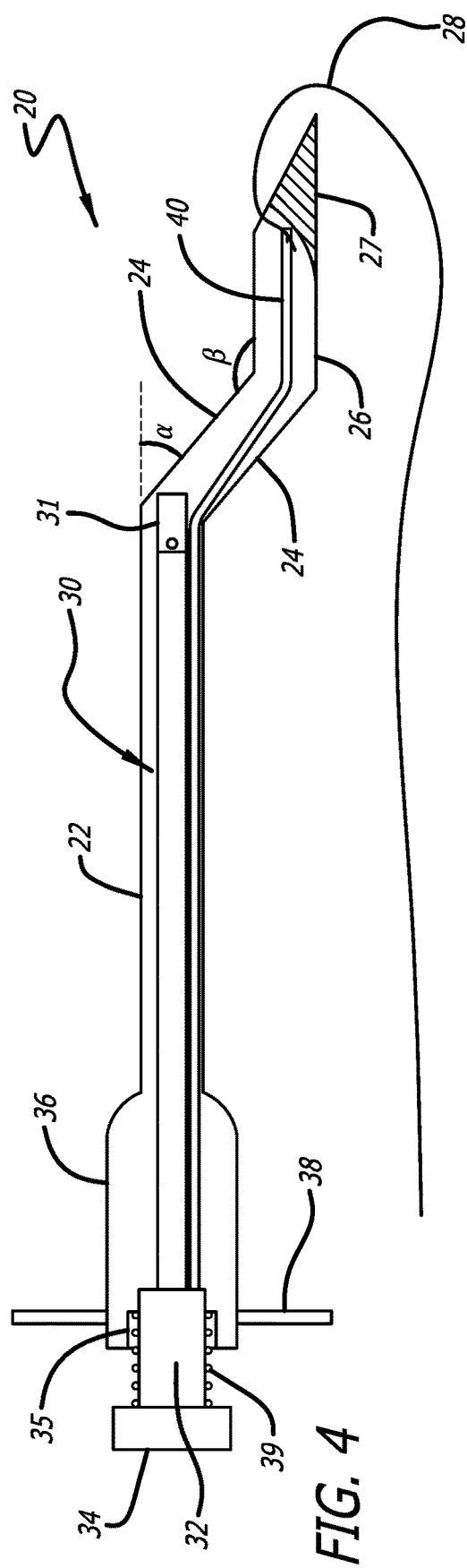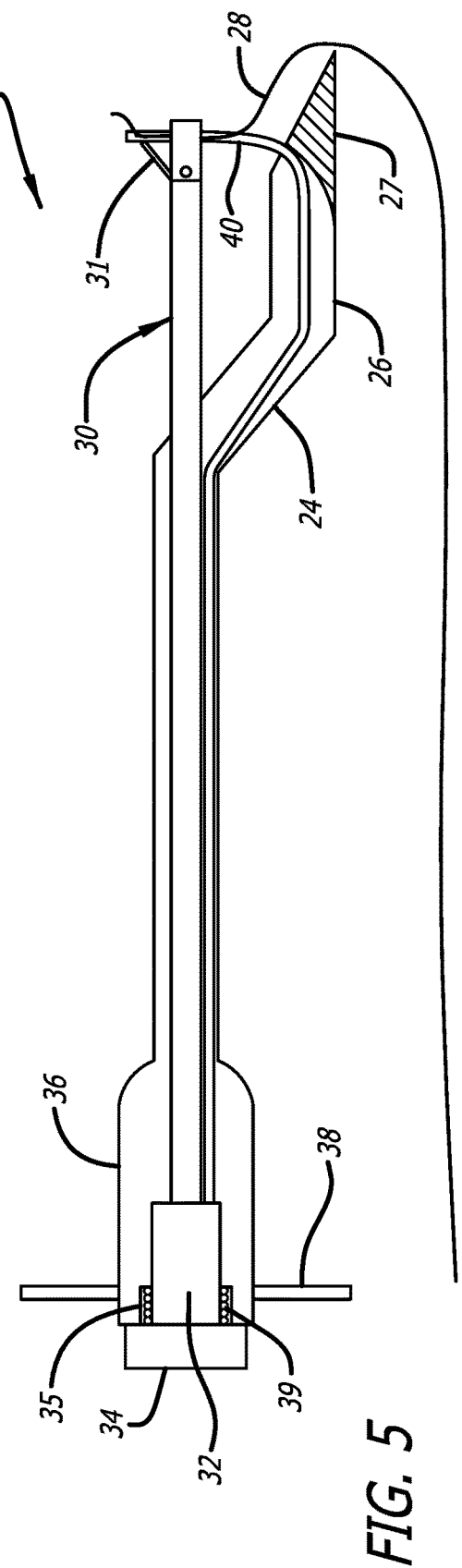

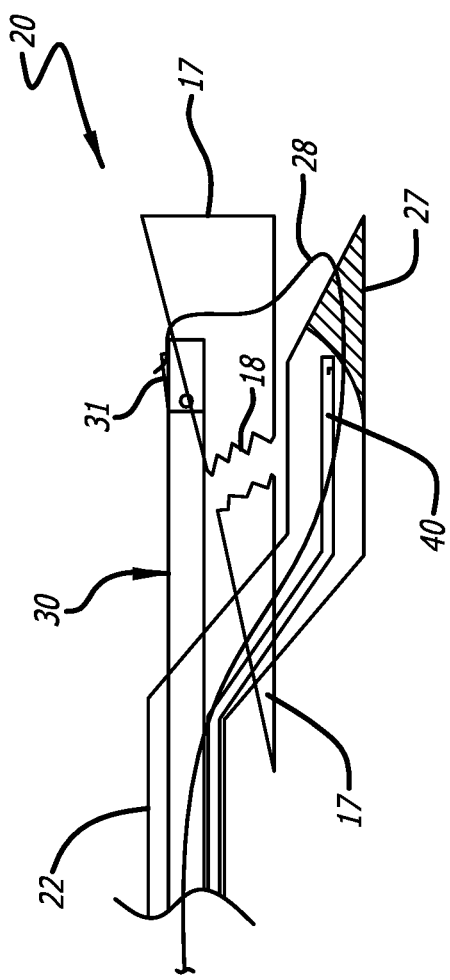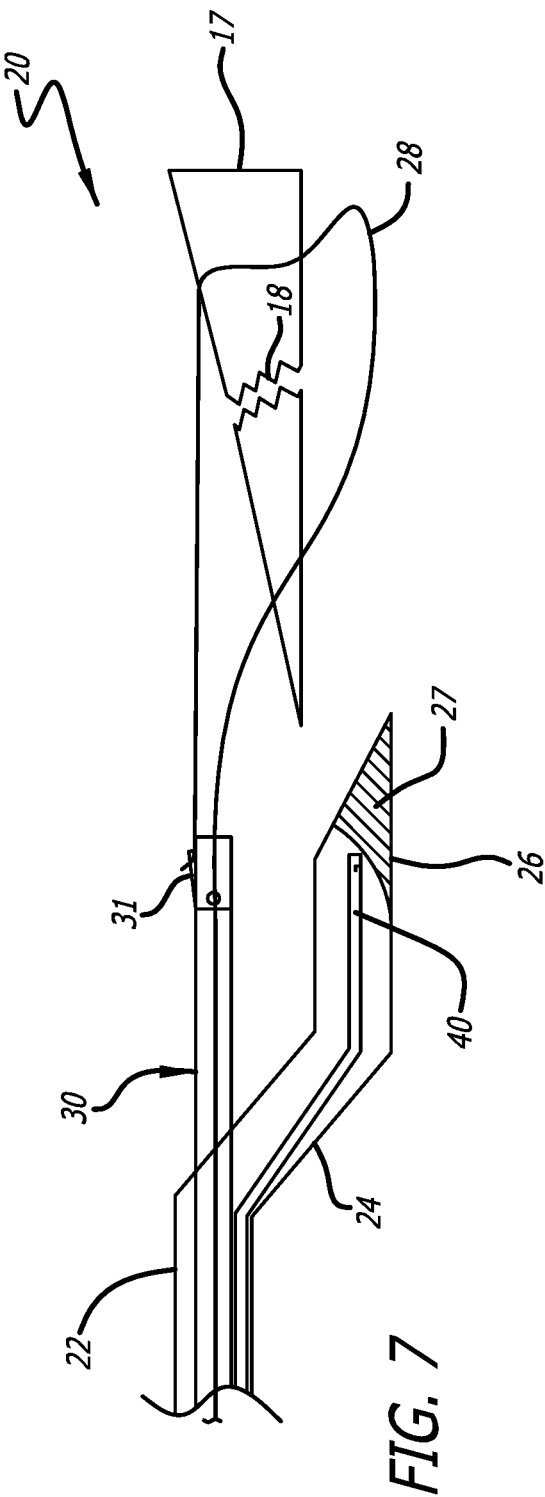

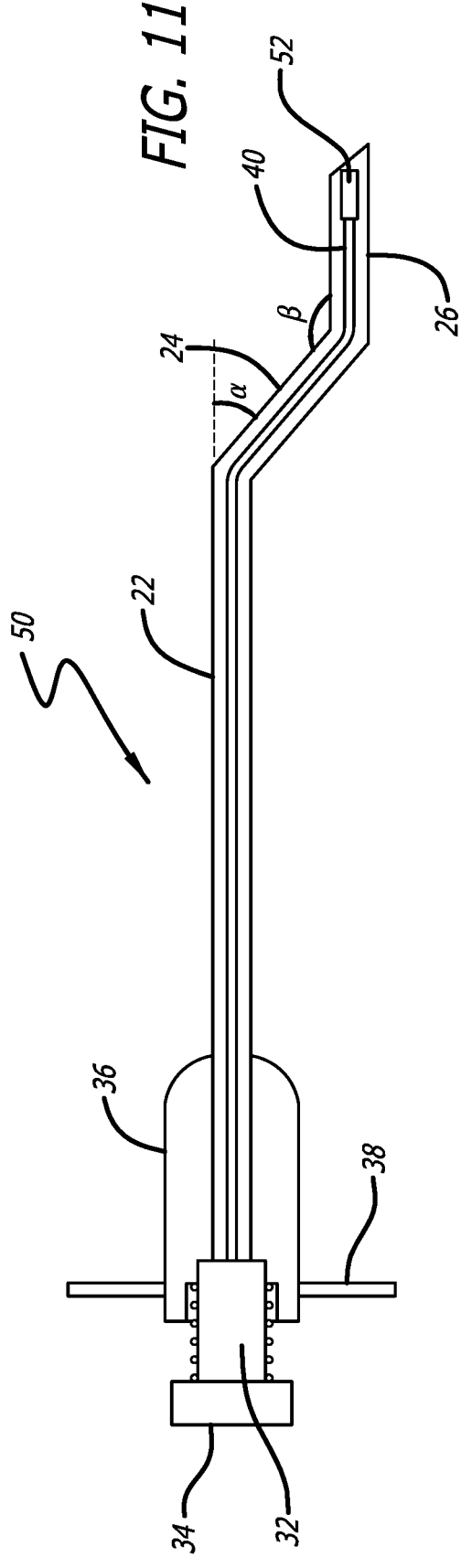

Z-SHAPED MENISCUS REPAIR DEVICE AND METHOD

REFERENCE TO RELATED APPLICATION

This application claims priority from a Provisional Application entitled Repair Device, filed Jun. 26, 2019, by R. Gabriel, application No. 62/867,170.

BACKGROUND OF THE INVENTION

Field of the Invention

The present invention relates to medical devices and apparatus. More specifically, the present invention relates to devices, methods and apparatus for repairing torn meniscus tissue and other such applications.

Description of the Related Art

"Arthroscopic management of meniscal injury is the most commonly performed orthopedic procedure in the United States annually. Many studies have demonstrated the long-term sequelae of partial and complete meniscectomy, and as a result, the use of meniscus repair has increased." See *Meniscal Repair* by published Catherine Laible, M D, et al. in the Journal of the American Academy of Orthopaedic Surgeons April 2013, Vol 21, No 4, pp. 204-213.

As pointed out by Laible et al.: "Historically, treatment of meniscus tears consisted of complete meniscectomy. Over the past few decades, however, the long-term morbidities of meniscal removal, namely the early development of knee osteoarthritis, have become apparent. Thus, management of meniscal tears has trended toward meniscal preservation. Recent technological advances have made repairs of the meniscus easier and stronger. In addition, adjunctive therapies used to enhance the healing process have advanced greatly in the past few years. Today, with increased understanding of the impact of meniscal loss and the principles of meniscal repair and healing, meniscal preservation is viewed as an increasingly realistic and important goal in the management of meniscus tears." (See ibid, Summary p. 211.)

The current best practice methodology for meniscal repair calls for a meniscus tear to be sewn vertically during arthroscopic surgery. However, this operation can be challenging for advanced tears inside the knee. Accordingly, special meniscal repair devices have been developed to facilitate the meniscus repair operation. One well-known device is the Knee Scorpion Suture Passer by Arthrex. See U.S. Pat. No. 8,460,318 issued Jun. 11, 2013 to Murray et al. and entitled SUTURING INSTRUMENT AND METHOD FOR PASSING MULTIPLE SUTURES, the teachings of which are hereby incorporated herein by reference. See also http://www.arthrex.com/knee/knee-scorpion and https://www.youtube.com/watch?v=Dh6JDZ8kYOk&feature=youtu.be Unfortunately, conventional meniscus repair devices are typically curved or straight making it difficult to get to hard to reach places in the knee joint to effect the repair.

Hence, a need remains in the art for an improved meniscal repair device that is more readily adapted to allow access to hard to reach places in the knee despite the angles therein.

SUMMARY OF THE INVENTION

The need in the art is addressed by the z-shaped surgical device of the present invention. In the illustrative embodiment, the device includes a handle and a rod secured to the handle having: a first elongate segment at a proximal end thereof; a second elongate segment angled with respect to the first segment; and a third elongate segment angled with respect to the second segment.

In the illustrative application, the invention provides an arthroscopic meniscus tissue repair suture passer device that penetrates tissue with its distal tip in one direction and utilizes a needle or similar part to penetrate tissue in the opposite direction placing a suture around the torn tissue. The device has an extended z-shaped shape distally that facilitates placement of a suture around torn meniscus tissue with a novel single stroke relative to the prior art. The z-shaped angles are extended for improved access, maneuverability and passage of the device to and through tissue including but not limited to meniscus and other tissue, around meniscus and other tissue, into open and tight spaces between joints and other bodily spaces, and in difficult to access spaces in joints and other compartments.

The z-shaped angles may be moveable and able to change from full flexion to extension of 180 degrees or greater and back and forth separately or together as a unit via a mechanical trigger. The z-shaped may be static, partially movable, or fully movable. The z angles may be curved or acute angles.

The device has a tissue penetrating distal tip that may be straight, curved or angled. The distal section may be rounded and at least partially hollow. The device may or may not have a handle. The device may utilize a guide to position the device in the body. The device may or may not be disposable. The distal device may be modified to deploy sutures, suture anchors, anchors, staples or other repair products as indicated. The repair products may or may not be biodegradable.

The self-contained device with single pass self-tying suture placement allows easily reproducible meniscus repairs that provide ordinary surgeons the ability to repair as oppose to resect meniscus tears arthroscopically. The ability of the device to measure depth provides increased safety from injury to posterior meniscus structures including nerves and blood vessels resulting from too deeply placed suture anchors and sutures. The penetrating tip with depth protection allows suture repair of far peripheral meniscus tears.

BRIEF DESCRIPTION OF THE DRAWINGS

FIG. 4 is an elevated sectional side view of the surgical device of the present invention in the pre-triggered mode of operation illustrated in FIG. 2.

FIG. 5 is an elevated sectional side view of the surgical device of the present invention in the post triggered mode of operation illustrated in FIG. 3.

FIG. 6 is a fragmented magnified sectional view of the distal end of the surgical device of the present invention in the second post insertion and post triggered position in which a suture has been fed around a tear in a meniscus in accordance with the teachings of the present invention.

FIG. 7 is a fragmented magnified sectional view of the distal end of the surgical device of the present invention in a third post insertion position in which a tear in a meniscus has been pulled closed by the application of tension to a suture through the surgical device of the present invention.

FIG. 11 is an elevated sectional side view showing an alternative anchor pusher embodiment of the present invention.

FIG. 12 is an elevated sectional side view showing an alternative anchor pusher embodiment of the present invention in an illustrative meniscus tear application in a first position thereof by which it places an anchor in a meniscus in the vicinity of a tear.

DESCRIPTION OF THE INVENTION

Illustrative embodiments and exemplary applications will now be described with reference to the accompanying drawings to disclose the advantageous teachings of the present invention.

While the present invention is described herein with reference to illustrative embodiments for particular applications, it should be understood that the invention is not limited thereto. Those having ordinary skill in the art and access to the teachings provided herein will recognize additional modifications, applications, and embodiments within the scope thereof and additional fields in which the present invention would be of significant utility.

Figure 1:
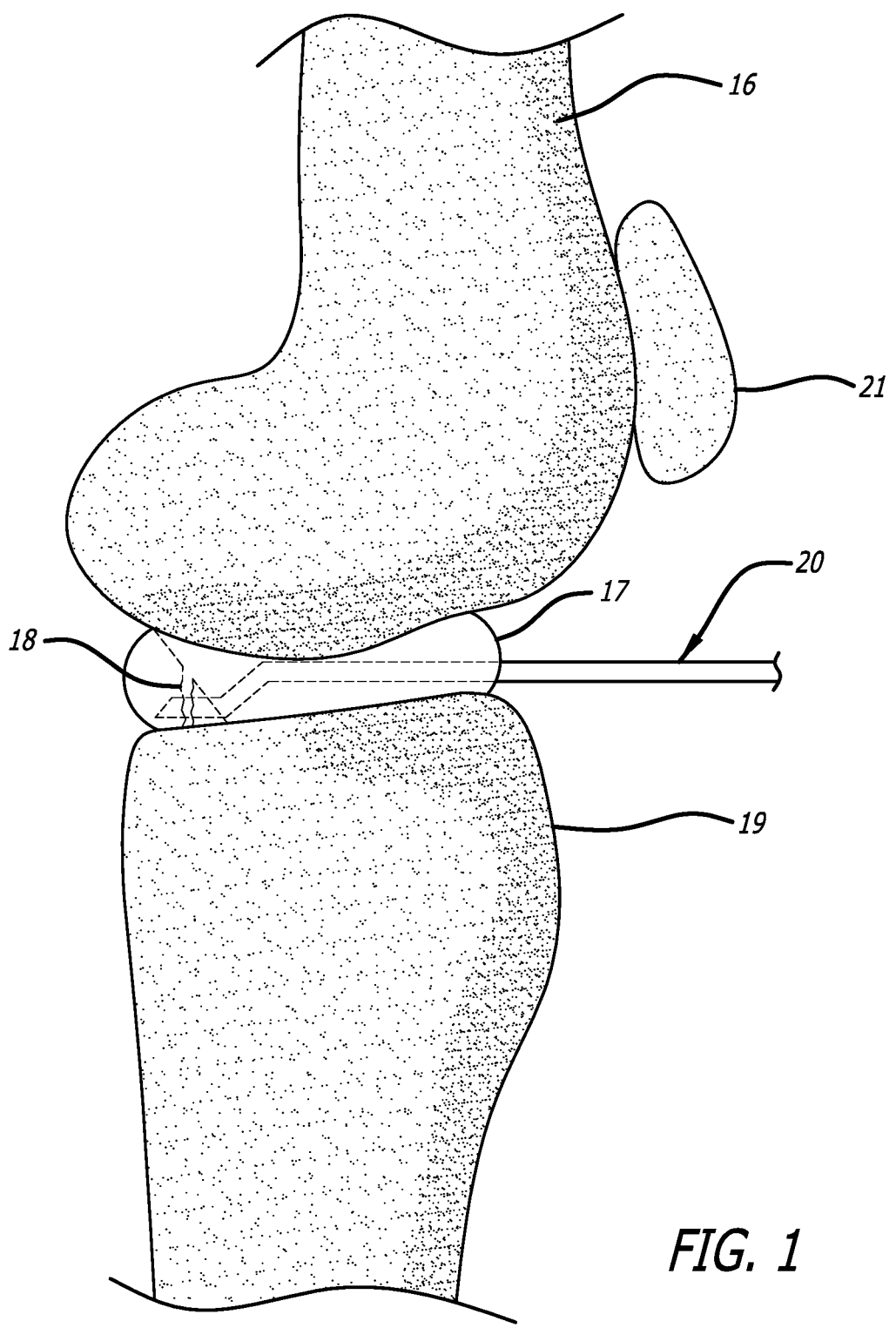
FIG. 1 is a diagram showing an illustrative embodiment of the surgical device of the present invention in connection with meniscal tear repair knee surgery operation.

FIG. 1 is a diagram showing an illustrative embodiment of the surgical device of the present invention in connection with meniscal tear repair knee surgery operation. In FIG. 1, the surgical device 20 of the present invention is shown inserted into a meniscus 17 between a femur 16 and tibia 19 below the patella 21.

Figure 2:
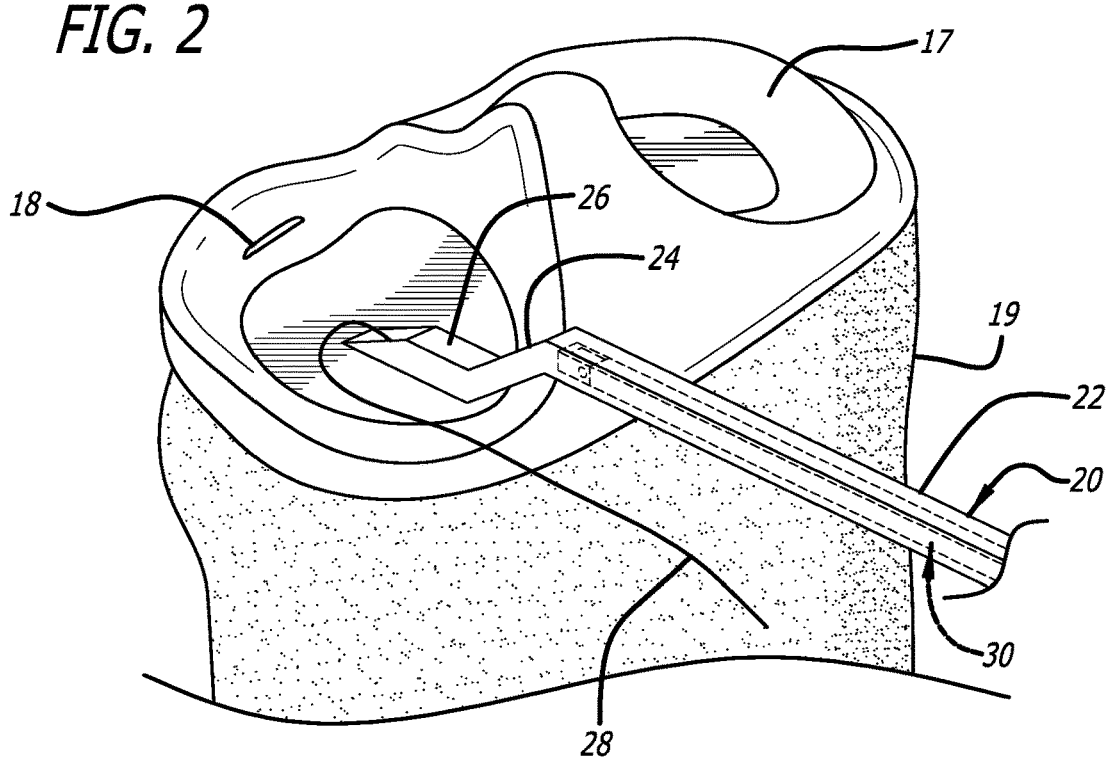
FIG. 2 is a diagram showing the illustrative application of the invention depicted in FIG. 1 with the femur removed to show the meniscus in the knee and the surgical repair device of the invention in a first pre-insertion and pre-triggered mode of operation therein.

FIG. 2 is a diagram showing the illustrative application of the invention depicted in FIG. 1 with the femur removed to show the meniscus in the knee and the surgical repair device 20 of the invention in a first pre-insertion and pre-triggered mode of operation therein.

Figure 3:
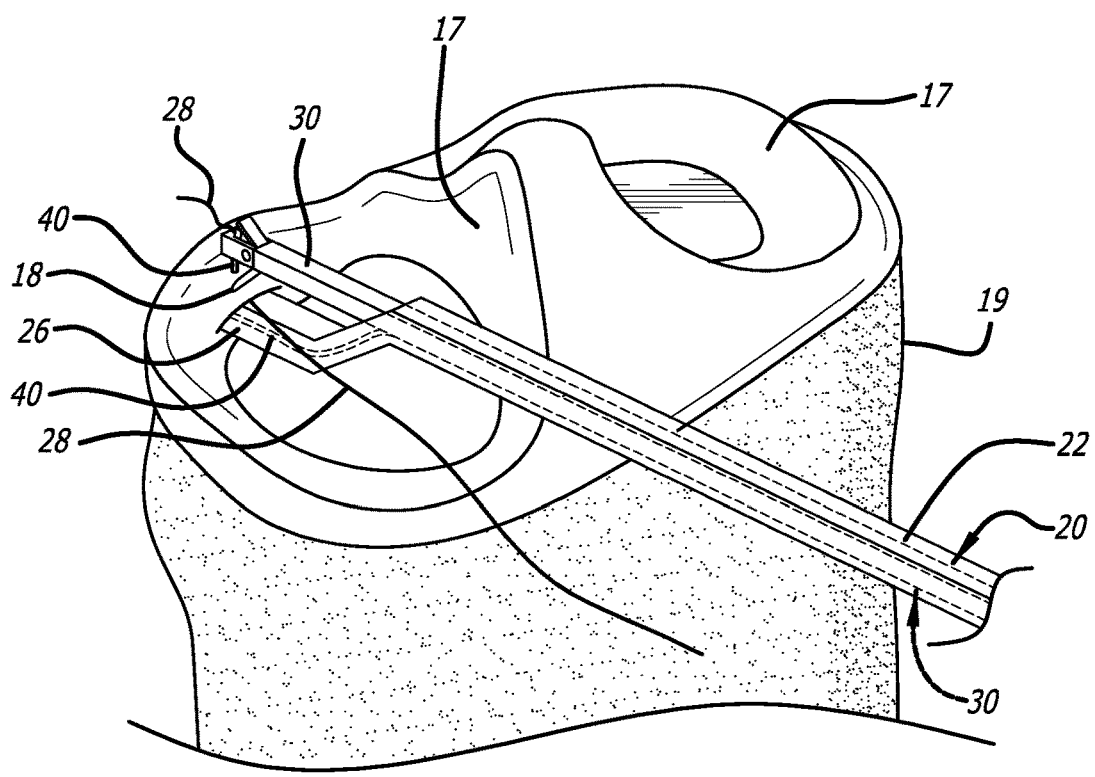
FIG. 3 is a diagram showing the illustrative application of the invention depicted in FIG. 2 with the surgical repair device of the invention in a second post-insertion and post triggered mode of operation.

FIG. 3 is a diagram showing the illustrative application of the invention depicted in FIG. 2 with the surgical repair device of the invention 20 in a second post-insertion and post triggered mode of operation.

FIG. 4 is an elevated sectional side view of the surgical device of the present invention in the pre-triggered mode of operation illustrated in FIG. 2.

FIG. 5 is an elevated sectional side view of the surgical device of the present invention in the post triggered mode of operation illustrated in FIG. 3.

FIG. 6 is a fragmented magnified sectional view of the distal end of the surgical device of the present invention in the second post insertion and post triggered position in which a suture has been fed around a tear in a meniscus in accordance with the teachings of the present invention.

As shown in FIGS. 2-5, the device 20 has a first elongate hollow rectangular cylindrical section 22 at a proximal end thereof, a second elongate hollow rectangular cylindrical section 24 coupled to the first section 22 at an approximate angle ($\alpha$) of −20-30 degrees relative to the horizontal, and a third elongate hollow rectangular cylindrical section 26, coupled to the second section 24 at an approximate angle ($\beta$) of 150-160 degrees relative to the horizontal, whereby the first, second and third sections in combination provide a longitudinal z-shaped arrangement.

A recipient arm 30 is mounted within the first section 22. The recipient arm is coupled to a trigger mechanism comprising a plunger 32, a trigger 34 and a handle 38 held in an initial first open position by a coil spring 39. The spring 39 is mounted in a cavity 35 in a collar 36 between the proximal end of the collar 36 and the trigger 34. The operation of a recipient arm is disclosed generally in the above-referenced U.S. Patent to Murray (U.S. Pat. No. 8,460,318), the teachings of which have been incorporated herein by reference. The suture 28 may be of conventional design and construction.

A needle 40 is also mounted within the first, second and third sections 22, 24 and 26. The first and third sections have open distal ends.

As shown in FIGS. 2 and 4, in a first pre-triggered mode of operation, the recipient arm 30 is retracted and maintained within the first section 22.

As shown in FIGS. 3 and 5, in the second mode of operation, when the device 20 is triggered by the application of pressure to the trigger 34 while holding the handle 38, the open distal end of the first section 22 enables the recipient arm 30 to translate out of the first section 22. Simultaneously, the needle 40 translates within the first, second and third sections 22, 24 and exits the open distal end of the third section 26 in an upward vertical direction while pulling the suture 28 as shown in FIG. 4.

In accordance with the present invention, the needle 40 is flexible, at least at the distal end thereof, such that as it translates against a ramp 27, it is deflected upwardly toward the recipient arm, carrying the suture 28 as shown in FIG. 5.

As shown in the fragmented magnified sectional view of FIGS. 5 and 6, the suture 28 is passed off to the recipient arm 30, captured and held by a trap door 31. The trap door 31 may be placed at the top of the distal end of the recipient arm 30 as shown, at the bottom of the distal end of the recipient arm 30 or within the body of the distal recipient arm 30.

Those of ordinary skill in the art can appreciate that a key feature of the invention is due to the fact that the inventive surgical device 20 enables the suture 28 to be more easily placed under and around the tear 18 in the meniscus 17 relative to the placement afforded by conventional devices and tools for effecting meniscus repairs. The z-shaped may be rotated placing the distal tip superiorly and recipient arm inferiorly passing the suture needle from top-to-bottom. The z-shaped device has arms extending distally that may be retracted, extended, fixed, movable, straight, angled, or curved. The device places a suture around torn meniscus tissue by utilizing the z-shaped device penetrating tip passing it manually through the meniscus tissue before or proximal to the tear then advancing the device past the tear then passing the suture through the meniscus tissue past or distal to the tear with the suture needle. The device may be effectively utilized to place a suture around meniscus or other tissue without penetrating the tissue proximal to the tear if adequate tissue is not available.

The device including the suture needle, arms, and other working parts may be deployed through the use of a proximal trigger mechanism, squeeze, push, pull or automated part.

After the device 20 is triggered and the suture is passed to the recipient arm, the trigger 34 is released and the recipient arm and the needle 40 are retracted by the action of the coil spring 39 within the cavity 35 in the handle 36 as shown in FIGS. 4 and 7. After the needle is retracted back into the device, the suture is left attached to the recipient arm. Tightening and knotting of the suture 28 then closes the tear as shown in FIGS. 7-10.

FIG. 7 is a fragmented magnified sectional view of the distal end of the surgical device of the present invention in a third post insertion position in which a tear in a meniscus has been pulled closed by the application of tension to a suture through the surgical device of the present invention.

Figure 8:
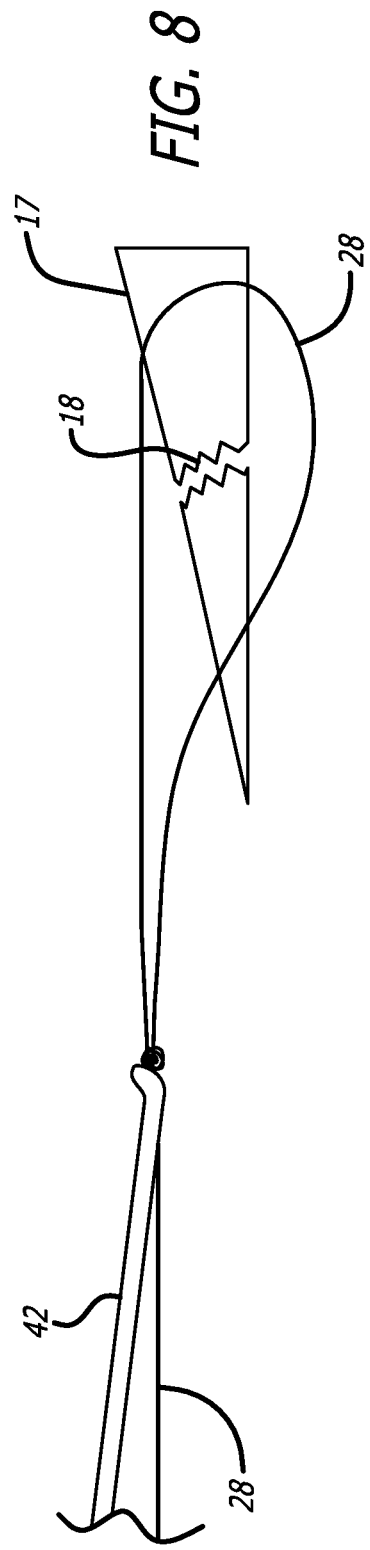
FIG. 8 is a diagram that illustrates the use of a knot pusher to tie a knot in the suture depicted in FIG. 7 and begin movement of the knot toward the repaired meniscus tear.

FIG. 8 is a diagram that illustrates the use of a knot pusher 42 to tie a knot in the suture depicted in FIG. 7 and begin movement of the knot toward the repaired meniscus tear.

Figure 9:
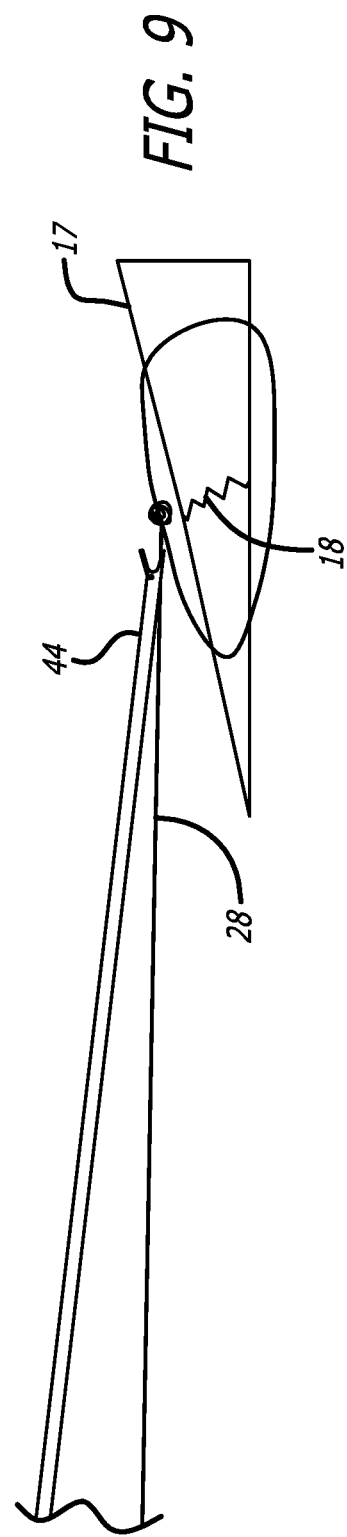
FIG. 9 shows the use of a cutter to cut the suture depicted in FIG. 8.

FIG. 9 shows the use of a cutter 44 to cut the suture 28 depicted in FIG. 8.

Figure 10:
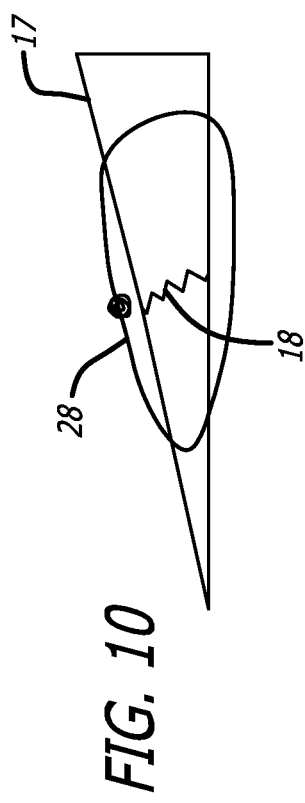
FIG. 10 is a diagram showing a meniscus tear repaired in accordance with the present teachings.

FIG. 10 is a diagram showing a meniscus tear repaired in accordance with the method of the present teachings.

In the best mode, the housing of the device 20 is constructed of metal, plastic or other suitable material. The needle and the recipient arm may be implemented in accordance with conventional teachings.

The first section should be 10 to 20 cm in length, 0.2 to 0.7 cm in width and 0.2 to 0.7 cm in height or 10 to 20 cm in length and 0.2 to 0.7 cm in diameter for a round embodiment. The second section should be 0.5 to 2 cm in length, 0.1 to 0.4 cm in width and 0.1 to 0.4 cm in height or 0.5 to 2 cm in length and 0.1 to 0.4 cm in diameter for a round embodiment. The third section should be 1 to 3 cm in length, 0.1 to 0.4 cm in width and 0.1 to 0.4 cm in height or 1 to 3 cm in length and 0.1 to 0.4 cm in diameter for a round embodiment. The first angle between the first and second sections should be 10 to 40 degrees (or radians) relative to the horizontal and the second angle should be 140 to 170 degrees (or radians) relative to the horizontal.

The device 20 can be implemented with hinges and locks so that the first and second angles are fully and independently adjustable from 1 to 180 degrees (or radians) relative to the horizontal as required for a given application. That is, the z-shaped angle may be adjustable from full flexion to extension of 180 degrees or greater separately or together as a unit and back and forth via the mechanical trigger to allow for increased maneuverability and access in the knee joint without departing from the scope of the present teachings.

Operation:

In operation, in a first embodiment, the arthroscopic z-shaped meniscus tissue repair device of the present invention facilitates repair of torn meniscus tissue by expedient, advantageous deployment and placement of a suture, suture anchor, anchor, staple or other products in key areas around a tear.

The suture 28 is placed around the meniscus tear 18 as follows. As the device 20 is inserted into the joint and triggered, the device initially penetrates the meniscus tissue 17 manually proximal to the meniscus tear 18 with its penetrating distal tip in one direction. The distal device tip 27 is manually advanced past the tear 18 inferior to the tear 18 transferring the suture from one side of the meniscus tissue to the other side.

When deployed and triggered, the device tip 27 penetrates the meniscus tissue in line with its direction straight ahead as the suture needle 40 penetrates the meniscus tissue 17 approximately 90 degrees from the direction of the device. This places the suture around the meniscus tear 18 with the extended z-shaped arm extending from the handle and collar 36 and 38. Simultaneously, the recipient arm 30 extends distally from the first section 22 to accept the suture 28 from the suture needle 40. This passes the continuous suture from the third section 26 to the recipient arm 30. The trigger is released retracting the recipient arm and the needle while maintaining tension on the suture. The suture is then knotted and cut.

Those of ordinary skill in the art can appreciate that the suture 28 is thus placed around the proximal and distal tissue of the tear with a single deployment or stroke of the device. This is significant inasmuch as, in accordance with conventional teachings, multiple strokes or deployments are required to place a continuous suture around both ends of a meniscus tear by initially placing a suture around one end then removing the suture passer from the knee, rethreading the device with the lower limb of the suture then passing the suture around the second end of the torn meniscus; or the device may allow the placement of the suture limb around one end of the tear and without removing the device from the knee but by repositioning and redeploying the device around the other end of the tear. Multiple deployments can be expected to increase the difficulty and time required for the procedure, increase the likelihood of further damaging the meniscus and increase the possibility of entangling sutures or placing them in an unworkable position requiring suture removal and a repeat repair attempt or aborting the repair attempt due to additional tissue damage from suture removal or needle redeployment.

In accordance with the present teachings, the z-shaped may be reversed placing the distal penetrating tip with the suture needle 40 on top and the extendable recipient arm on the bottom. The suture is transferred initially with the penetrating tip passed through the meniscus tissue from bottom-to-top following the path of the penetrating tip that starts beneath the meniscus then with the suture needle from top-to-bottom placing a suture around the torn tissue with the suture limbs exiting on the inferior surface of the meniscus.

The device can change its configuration by a mechanical trigger (not shown) from a position of full extension to a z-shaped type position and back and forth flexing at one or both z-shaped angles individually or together to form a z-shaped shape that incorporates a straight, hyperextension or other z-shaped configuration position that can be held statically or moved while being utilized to repair tissue.

The z shape may consist of curved z angles or acute z angles. The device may be fully contained with a preloaded needle and suture that place a self-tying suture or a suture that needs to be hand tied around a meniscus tear upon deployment without the need to reposition the device.

Alternative Embodiments

FIG. 11 is an elevated sectional side view showing an alternative anchor pusher embodiment of the present invention. In this embodiment, the recipient arm 30 is eliminated and the distal end of the first section 22 is closed but may house an extendable non-recipient superior arm to measure the distance to the back of the meniscus to protect against over penetration of the suture anchor.

FIG. 12 is an elevated sectional side view showing the alternative anchor pusher embodiment 50 of the present invention in an illustrative meniscus tear application in a first position thereof by which it places an anchor 52 in a meniscus 17 in the vicinity of a tear 18.

Figure 13:
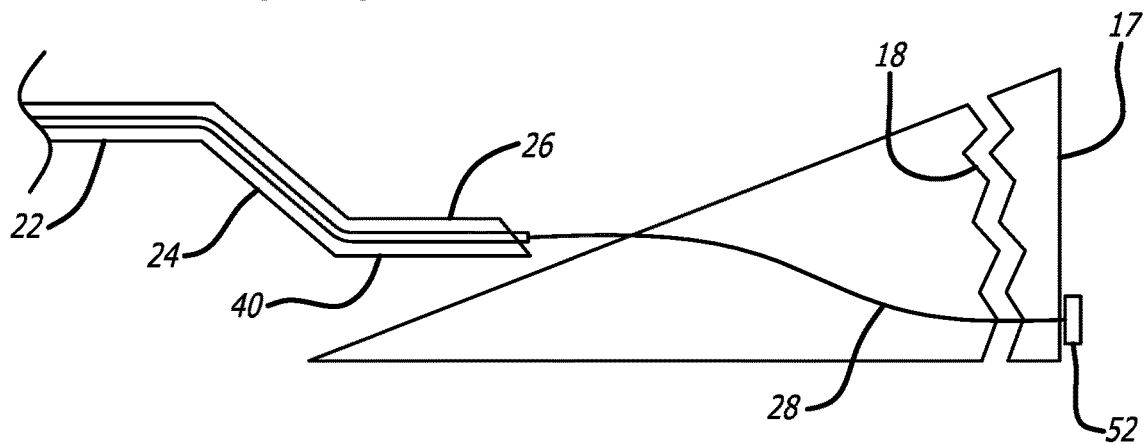
FIG. 13 is an elevated sectional side view showing the alternative anchor pusher embodiment of FIG. 12 in the illustrative meniscus tear application in a third position thereof set to receive a second anchor.

FIG. 13 is an elevated sectional side view showing the alternative anchor pusher embodiment 50 of FIG. 12 in the illustrative meniscus tear application in a third position thereof set to receive a second anchor.

Figure 14:
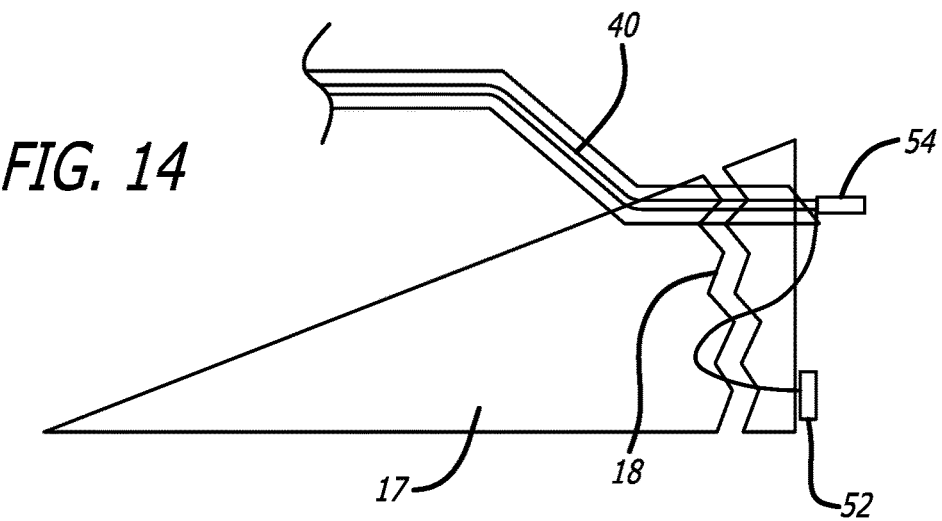
FIG. 14 is an elevated sectional side view of FIG. 13 showing the alternative anchor pusher embodiment in a fourth position thereof by which it places a second anchor in a meniscus in the vicinity of a tear.

FIG. 14 is the elevated sectional side view of FIG. 13 showing the alternative anchor pusher 50 embodiment in a fourth position thereof by which it places a second anchor 54 in a meniscus 17 in the vicinity of a tear 18.

As shown in FIGS. 11-14, the inventive anchor pusher 50 places a suture around or across a meniscus tear with an anchor attached to a single suture or multiple sutures. The device may contain one or more suture anchors in the at least partially hollow section 26 of the distal end of the z-shaped device 50. The suture anchors may be placed into the meniscus tissue in a top-to-bottom or bottom-to-top or side-to-side configuration.

In operation, the device 50 is passed through the meniscus by penetrating the meniscus tissue proximal to a meniscus tear or may be passed under or around torn meniscus tissue and advanced across the meniscus through the base or periphery of the meniscus to the outer wall. The device 50 may be passed through the substance or tissue of the meniscus at its peripheral attachment. The device 50 is advanced through to the outer wall of the peripheral meniscus and the suture anchor is deployed from the distal device with a proximal trigger that may be a push, slide, pull or other. The device may utilize a suture with two attached anchors deploying the anchors on opposite sides of a meniscus tear and securing the suture with a self-tying knot or locking anchor.

If used with a single anchor 52 after deployment of the suture anchor 52, the device 50 is removed and the suture 28 remains attached by the anchor 52 to the outer aspect of the meniscus. The tear may be repaired by placing a second suture anchor 52 on the opposite side from the first and tying the sutures by hand with a surgical knot pusher or securing the two sutures with a locking anchor or other device.

After placement of a single suture anchor 52 the suture may be secured across the meniscus tear by threading the suture 28 through a locking free anchor 54 passed down the suture limb to the opposite side of the meniscus tear. The free anchor passer may or may not be z-shaped shaped and may be straight, angled or curved. After placement of a single suture anchor the suture may be secured across the meniscus tear with a non-locking free anchor on the outer wall secured by a suture-locking anchor on the inner aspect of the meniscus or it may be tied with a second suture when using a multiple limb suture anchor. After placement of a single suture anchor the suture may be secured across the meniscus tear by locking the suture onto a free anchor passed to the outer wall secured with a self-tying suture between the two anchors.

Figure 15:
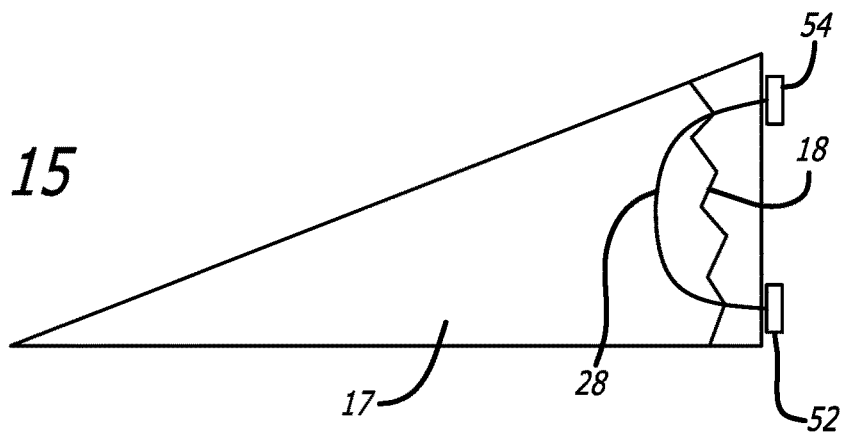
FIG. 15 is a diagram showing the meniscus of FIGS. 12-14 fully repaired utilizing the present teachings.

FIG. 15 is a diagram showing the resulting meniscus tear 18 fully repaired utilizing the present teachings.

In the best mode, the device 50 is constructed of metal, plastic or other suitable material. The first section should be 10 to 20 cm in length, 0.2 to 0.7 cm in width and 0.2 to 0.7 cm in height or 10 to 20 cm in length and 0.2 to 0.7 cm in diameter for a round embodiment. The second section should be 0.5 to 2 cm in length, 0.1 to 0.4 cm in width and 0.1 to 0.4 cm in height or 0.5 to 2 cm in length and 0.1 to 0.4 cm in diameter for a round embodiment. The third section should be 1 to 3 cm in length, 0.1 to 0.4 cm in width and 0.1 to 0.4 cm in height or 1 to 3 cm in length and 0.1 to 0.4 cm in diameter for a round embodiment. The first angle between the first and second sections should be 10 to 40 degrees (or radians) relative to the horizontal and the second angle should be 140 to 170 degrees (or radians) relative to the horizontal.

The device 50 can be implemented with hinges and locks at the angles so that the first and second angles are fully and independently adjustable from 1 to 180 degrees (or radians) relative to the horizontal as required for a given application. The anchor and or suture may or may not be biodegradable.

In short, in the illustrative application, the invention is an arthroscopic meniscus tissue repair suture passer device that penetrates tissue with its distal tip in one direction and utilizes a needle or similar part to penetrate tissue in the opposite direction placing a suture around the torn tissue. The device may be used to repair torn meniscus tissue and to repair other soft tissue tears and defects elsewhere in the body utilizing a top-to-bottom or bottom-to-top or side-to-side suture configuration.

The suture and needle may be pre-loaded, housed and or self-contained in the device or may require that the suture be manually loaded onto the needle. The device arms may be rounded and at least partially hollow with a penetrating distal tip that allows penetration of the device through tissue and a needle or similar structure in the distal section that extends from the device to penetrate tissue. The device may utilize a fixed or movable superior or inferior section that may partially or completely extend, retract and or move up and down from a fixed point or along the slope of the z-shaped angle and may retract after deployment. The device may have self-tying sutures or may require that the sutures be tied by hand utilizing a knot pusher or other device. The device may utilize a movable part attached to the superior and or inferior section to facilitate passage of the device through tissue. The device may or may not have an attached handle.

In an alternative embodiment, the z-shaped meniscus suture anchor repair device 50 has a tissue-penetrating z-shaped distal section housing a deployable suture anchor. When deployed and triggered, the device 50 places the suture anchor 52 around or across a meniscus tear 18.

The trigger releases the anchor from the device leaving it anchored to the outer wall as the device is backed out of the meniscus. The anchored suture 52 spans the meniscus tear from distal to proximal exiting the surface of the meniscus. Without removing the device from the knee, a second anchor 54 is attached to the suture and advanced on the opposite side of the meniscus tear through the meniscus tissue to the outer wall and is deployed in a similar fashion. The device 50 is backed out of the knee and the suture is secured with a self-tying knot with the suture spanning the tear and repairing the meniscus.

Those having ordinary skill in the art and access to the present teachings will recognize additional modifications, applications and embodiments within the scope thereof.

It is therefore intended by the appended claims to cover any and all such applications, modifications and embodiments within the scope of the present invention.

The invention claimed is:
1. A surgical device comprising:
a handle;
a rod secured to the handle having:

a first elongate linear segment at a proximal end thereof;

a second elongate linear segment angled with respect to the first segment;

a third elongate linear segment angled with respect to the second segment;

a recipient arm mounted within the first elongate segment; and an element adapted to penetrate tissue mounted for reciprocal movement within the first, second and third segments.

2. The invention of claim 1 wherein said element adapted to penetrate tissue mounted within the first, second and third segments is a needle.

3. The invention of claim 1 further including a trigger mounted within the handle.

4. The invention of claim 3 further including an element adapted to penetrate tissue mounted within the first, second and third segments and coupled to the trigger.

5. The invention of claim 4 wherein said element is a needle adapted to translate within the first, second and third segments upon an application of pressure to the trigger.

6. The invention of claim 4 further including a recipient arm mounted within the first elongate segment and coupled to the trigger.

7. The invention of claim 6 wherein the recipient arm is adapted to translate within the first segment upon an application of pressure to the trigger.

8. The invention of claim 6 wherein the needle and the recipient arm are adapted to translate upon the application of pressure to the trigger.

9. The invention of claim 8 wherein the needle is adapted to deliver a suture to the recipient arm when fully extended.

10. The invention of claim 9 further including the suture.

11. The invention of claim 9 wherein the needle may enter the recipient arm from distal to proximal to deliver the suture.

12. The invention of claim 9 wherein the recipient arm provides depth measurements whether or not it accepts sutures.

13. The invention of claim 1 wherein the second segment is angled relative to the first segment at an approximate angle α of 20-30 degrees.

14. The invention of claim 13 wherein the third segment is angled relative to the second segment at an approximate angle β of 150-160 degrees.

15. A method for repairing torn tissue including the steps of:

loading a suture into a surgical device comprising:
a handle;
a rod secured to the handle having:
a first elongate linear segment at a proximal end thereof;
a second elongate linear segment angled with respect to the first segment;
a third elongate linear segment angled with respect to the second segment;
a recipient arm mounted within the first elongate segment; and
an element adapted to penetrate tissue mounted for reciprocal movement within the first, second and third segments and inserting device into the tissue to effect the repair.

16. The method of claim 15 wherein the device further includes a needle mounted in the recipient arm triggered to pass the suture to the recipient arm after the device is inserted into the tissue and triggered.

17. The method of claim 16 further including the step of removing the device after it is triggered leaving the suture around a tear.

18. The method of claim 17 further including the step of removing the device, knotting the suture and cutting the suture.

19. A method of inserting anchors into tissue including the steps of:

loading an anchor into a surgical device comprising:
a handle and
a rod secured to the handle having:
a first elongate linear segment at a proximal end thereof;
a second elongate linear segment angled with respect to the first segment;
a third elongate linear segment angled with respect to the second segment and;
an element adapted to penetrate tissue mounted for reciprocal movement within the first, second and third segments and inserting device into the tissue to deposit the anchor.

* * * * *